US006239180B1

(12) United States Patent
Robbins

(10) Patent No.: US 6,239,180 B1
(45) Date of Patent: *May 29, 2001

(54) TRANSDERMAL THERAPEUTIC DEVICE AND METHOD WITH CAPSAICIN AND CAPSAICIN ANALOGS

(75) Inventor: Wendye R. Robbins, San Mateo, CA (US)

(73) Assignee: The Regents of the University of California, Oakland, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/990,633

(22) Filed: Dec. 15, 1997

Related U.S. Application Data

(63) Continuation-in-part of application No. 08/746,207, filed on Nov. 6, 1996
(60) Provisional application No. 60/006,385, filed on Nov. 8, 1995.

(51) Int. Cl.[7] ............................. A01N 37/18; A61K 31/16
(52) U.S. Cl. .............................................................. 514/627
(58) Field of Search ............................................. 514/627

(56) References Cited

U.S. PATENT DOCUMENTS

| | | | |
|---|---|---|---|
| 4,313,958 | 2/1982 | LaHann | 424/324 |
| 4,424,205 | 1/1984 | LaHann et al. | 424/72 |
| 4,486,450 | 12/1984 | Bernstein | 424/324 |
| 4,532,139 | 7/1985 | Janusz et al. | 514/627 |
| 4,536,404 | 8/1985 | Bernstein | 514/627 |
| 4,544,668 | 10/1985 | Janusz et al. | 514/563 |
| 4,544,669 | 10/1985 | LaHann et al. | 514/563 |
| 4,592,912 | 6/1986 | Nickolaus . | |
| 4,812,446 | 3/1989 | Brand | 514/165 |
| 4,898,887 * | 2/1990 | Janusz et al. | 514/617 |
| 4,971,800 | 11/1990 | Chess et al. | 424/449 |
| 4,997,853 | 3/1991 | Bernstein | 514/626 |
| 5,260,313 | 11/1993 | Frome | 514/552 |
| 5,290,816 | 3/1994 | Blumberg | 514/691 |
| 5,411,738 | 5/1995 | Hind | 424/445 |
| 5,431,914 | 7/1995 | Adekunle et al. | 424/401 |
| 5,589,180 | 12/1996 | Hind | 424/402 |
| 5,665,360 | 9/1997 | Mann | 424/195.1 |
| 5,665,378 | 9/1997 | Davis et al. | 424/448 |
| 5,709,869 | 1/1998 | Hind | 424/402 |
| 5,788,982 | 8/1998 | Nadoolman et al. | 424/440 |
| 5,854,291 | 12/1998 | Laughlin et al. | 514/626 |
| 5,856,361 | 1/1999 | Holt et al. | 514/627 |
| 5,869,533 | 2/1999 | Holt | 514/627 |
| 5,910,512 | 6/1999 | Conant | 514/617 |
| 5,962,532 | 10/1999 | Campbell et al. | 514/627 |

FOREIGN PATENT DOCUMENTS

| | | | |
|---|---|---|---|
| 90/14083 | 11/1990 | (WO) | A61K/31/335 |
| 91/08738 | 6/1991 | (WO) | A61K/31/165 |
| 93/17695 | 9/1993 | (WO) | A61K/35/78 |
| 96/40079 | 12/1996 | (WO) | A61K/9/24 |
| 98/40070 | 9/1998 | (WO) | A61K/31/47 |
| 99/37675 | 7/1999 | (WO) | C07K/14/435 |
| 99/43322 | 9/1999 | (WO) | A61K/31/44 |

OTHER PUBLICATIONS

Y.H. Tsai et al., "Development and Evaluation of Transdermal Patches of Nonivamide and Sodium Nonivamide Acetate," *Die Pharmazie*, Feb. 1997, vol. 52 pp. 135–138.
Craft and Porreca, Treatment Parameters of Desensitization to Capsaicin, *Life Sciences*, 51, pp. 1767–1775 (1992).
McMahon et al., "The Consequences of Long–Term Topical Capsaicin Application in the Rat," *Pain*, 44, pp. 301–310 (1991).
Toh et al., "The Pharmacological Actions of Capsaicin and Analogues," *British Journal of Pharmacology*, 10, pp. 175–182 (1955).
Geppetti et al., "Secretion, Pain and Sneezing Induced by the Application of Capsaicin to the Nasal Mucosa in Man," *British Journal of Pharmacology*, 93, pp. 509–514 (1988).
Jancsó et al., "The Role of Sensory Nerve Endings in Neurogenic Inflammation Induced in Human Skin and in the Eye and Paw of the Rat," *British Journal of Pharmacological Chemotherapy*, 32, pp. 32–14 (1968).
Watso et al., "Post–Herpetic Neuralgai and Topical Capsaicin," *Pain*, 33, pp. 33–340 (1988).
Scholten, "Ointments for Treating Painful Conditions—Containing Tincture of Capsicum," Abstract of DE 4,414,502 A1, Nov. 2, 1995.
Altymyshev et al., "Petroleum Jelly–Based Balsam Ointment—Containing Red Pepper Oil Extract and Spruce Resin Alcoholic Solution, with Camphor, Menthol, Lanolin and Paraffin," Abstract of SU 1,794,454 A1, Feb. 15, 1993.

\* cited by examiner

*Primary Examiner*—Dwayne C. Jones

(57) ABSTRACT

Transdermal application of capsaicin (or a capsaicin analog) in a concentration from greater than about 5% to about 10% by weight has been discovered to be an extremely effective therapy for treating neuropathic pain, so long as an anesthetic, preferably by means of a transdermal patch, is administered initially to the affected area to minimize the expected side effects from subsequent capsaicin application.

5 Claims, No Drawings

TRANSDERMAL THERAPEUTIC DEVICE AND METHOD WITH CAPSAICIN AND CAPSAICIN ANALOGS

CROSS-REFERENCE TO RELATED APPLICATIONS

This is a continuation-in-part application of Ser. No. 08/746,207, filed Nov. 6, 1996, which is an application based on provisional patent application Ser. No. 60/006,385, filed Nov. 8, 1995.

FIELD OF THE INVENTION

The present invention generally relates to peripheral neuropathy, and more particularly to treatments of neuropathic pain by use of capsaicin (and/or a capsaicin analog) administered transdermally in high concentration in conjunction with a previously administered anesthetic to the affected areas.

BACKGROUND OF THE INVENTION

Neuropathic pain is thought to occur because of a sensitization in the peripheral and central nervous systems after an initial injury to the peripheral system. Direct injury to the peripheral nerves as well as many systemic diseases including AIDS/HIV, Herpes Zoster, syphilis, diabetes, and various autoimmune diseases, can induce this disorder. Neuropathic pain is typically burning, shooting, and unrelenting in its intensity and can sometimes be more debilitating that the initial injury or the disease process which induced it. Unfortunately, the few remedies that have been reported to alleviate this condition are effective in only a small percentage of patients.

Capsaicin, a pungent substance derived from the plants of the Solanaceae family (hot chili peppers), has long been used as an experimental tool because of its selective action on the small diameter afferent nerve fibers, or C fibers, that are believed to mediate pain. From studies in animals, capsaicin appears to trigger C fiber membrane depolarization by opening cation selective channels for calcium and sodium. Although detailed mechanisms are not yet known, capsaicin mediated effects include: (I) activation of nociceptors in peripheral tissues; (ii) eventual desensitization of peripheral nociceptors to one or more stimulus modalities; (iii) cellular degeneration of sensitive unmyelinated C fiber afferents; (iv) activation of neuronal proteases; (v) blockage of axonal transport; and (vi) the decrease of the absolute number of C fibers without affecting the number of myelinated fibers.

Because of capsaicin's ability to desensitize nociceptors in peripheral tissues, its potential analgesic effects have been assessed in various clinical trials. However, since the capsaicin application itself frequently causes burning pain and hyperalgesia apart from the neuropathic pain being treated, patient compliance has been poor and the drop out rates during clinical trials have exceeded fifty percent. The spontaneous burning pain and heat hyperalgesia are believed to be due to intense activation and temporary sensitization of the peripheral nociceptors at the site of capsaicin application (primary hyperalgesia). Mechanical hyperalgesia evident in areas surrounding the site of topical application appears to originate from central sensitization of dorsal horn neurons involved in pain transmission (secondary hyperalgesia). Because of these side effects, the maximal capsaicin concentration used in previous human studies has usually been limited to 0.075%.

U.S. Pat. No. 5,431,914, issued Jul. 11, 1995, suggests that a topical preparation containing a concentration of capsaicin of about 0.01% to about 0.1% could be used to treat internal organ pathologies. U.S. Pat. No. 5,665,378, issued Sep. 9, 1997, discusses a transdermal therapeutic formulation comprising capsaicin, a non-steroidal anti-inflammatant, and pamadorm (a diuretic agent) where the composition is said to contain from about 0.001–5% by weight capsaicin and to be useful in treating the pain and discomfort associated with menstrual cramps, bloating, and/or muscular pain such as muscular back pain.

Analogs of capsaicin with physiological properties similar to capsaicin are known. For example, resiniferatoxin is described as a capsaicin analog by inventor Blumberg, U.S. Pat. No. 5,290,816, issued Mar. 1, 1994. Inventor Brand in U.S. Pat. No. 4,812,446, issued Mar. 14, 1989, describes capsaicin analogs and methods for their preparation. Further, inventors LaHann et al. in U.S. Pat. No. 4,424,205, issued Jan. 3, 1984, cite Newman, "Natural and Synthetic Pepper-Flavored Substances" published in 1954 as listing pungency of capsaicin-like analogs. Ton et al., *British Journal of Pharmacology*, 10, pp. 175–182 (1955) discuss pharmacological actions of capsaicin and its analogs.

SUMMARY OF THE INVENTION

In one aspect of the present invention, a transdermal delivery system is provided for administration of capsaicin (and/or a capsaicin analog) effective to alleviate the symptoms of peripheral neuropathy for prolonged period of time. Thus, a transdermal kit comprises at least one transdermal device, hereinafter referred to as a patch, which is conveniently applied to the skin to provide the capsaicin formulation. More preferably, the kit has two patches, one of which provides anesthesia and the other the capsaicin formulation. The use of the transdermal drug delivery system produces increased patient compliance. Further, the transdermal delivery of capsaicin is most desirable for reasons of convenience and effectiveness.

In another aspect of the present invention, a therapeutic method comprises administering a suitable anesthetic to a patient suffering neuropathic pain followed by applying a composition including from greater than about 5% to about 10% of capsaicin (and/or a capsaicin analog) by weight to the patient. The anesthetic preferably is administered transdermally. The capsaicin (and/or capsaicin analog) containing composition is administered transdermally and includes a vehicle with skin penetrating properties.

The prior administration of a suitable anesthetic sufficiently desensitizes C fibers to the expected side effects of the subsequent capsaicin application. The administration of the anesthetic together with the subsequent administration of a high concentration of capsaicin appears to alleviate the symptoms of peripheral neuropathy for a prolonged period of time extending several weeks to months.

DETAILED DESCRIPTION OF THE PREFERRED EMBODIMENTS

Practice of the invention prevents the burning pain and hyperalgesia to both heat and touch typically occurring after even the relatively low concentration applications of capsaicin ointment known to the art. Such burning pain is avoided by first administering an anesthetic, so as to cause regional anesthesia in the areas to be treated. Preferred regional anesthetic agents are sodium channel blockers. A variety of sodium channel blocking anesthetics are known and useful, such as Lidocaine, tetracaine, bupivicaine and chloroprocaine.

Effective anesthesia for subsequent capsaicin application can be accomplished by lumbar, epidural catheter, or blockage of the major peripheral nerves of the affected area. However, more preferably the suitable anesthetic is administered transdermally, such as by a patch device to the entire area which will be treated and left in place for a sufficient period of time so as to block C fiber heat transmissions. Such topical agents such as tetracaine (Amethocaine™) or a Eutectic mixture of Lidocaine and Prilocaine (ELMA™) can perform this objective.

When the anesthetic administered has taken effect in providing analgesia, then a composition including capsaicin (and/or a capsaicin analog) is administered, preferably by transdermal application, at least once. This composition preferably is formulated with a vehicle having a skin penetrating and skin absorbing agent. One suitable such vehicle is commercially available as velvachol (Galderma).

The topical application of the capsaicin (and/or capsaicin analog) containing composition delivers the drug through the skin. Because skin is a structurally complex, relatively thick membrane, molecules moving from the environment into and through intact skin must first penetrate the stratum corneum and any material on its surface, then penetrate the viable epidermis, the papillary dermis, and the capillary walls. To be so absorbed, molecules must overcome a different resistance to penetration in the different types of tissue. It is for these reasons that the formulation is prepared so as to increase skin permeability and to increase the permeability in particular of the stratum corneum. Such skin penetrating and absorbing agents are known to the art. For example, the capsaicin composition can include one or more penetration-enhancing agents such as those described by U.S. Pat. No. 4,971,800, issued Nov. 20, 1990, inventors Chess et al.

At present, capsaicin is commercially available in over-the-counter topical preparations at concentrations of 0.025% and 0.075%. However, capsaicin concentrations in the range of greater than about 5% up to about 10% appear to be necessary to sufficiently desensitize the C fiber population to effectuate prolonged relief from many of the symptoms of peripheral neuropathy. Thus, capsaicin compositions necessary for the practice of this invention must be prepared by mixing pure capsaicin powder to the desired concentration by weight, from greater than about 5% to 10%, more preferably at about 7.5%, in the selected vehicle. Such an admixture of high concentration of capsaicin is a substance that must be handled with care and preferably is prepared by a skilled technician or a trained pharmacist. Where a capsaicin analog is selected to replace some or all of the capsaicin, then the analog can be selected from those analogs with similar physiological properties to capsaicin as are known to the art.

Preferably, the transdermally effective composition is utilized to prepare a "reservoir type" or "matrix type" patch which is applied to the skin and worn for a specific period of time to permit the penetration of a desired amount of the capsaicin formulation through the skin. Most preferably, the patches of the invention will be worn for a total period of about 4 hours and provide a total of 1 hour exposure to 7.5% of capsaicin.

The capsaicin formulations can be packaged to produce a "reservoir type" transdermal patch with or without a rate-limiting patch membrane. The size of the patch and or the rate limiting membrane can be chosen to deliver the transdermal flux rates desired. Such a transdermal patch can consist of a polypropylene/polyester impervious backing member heat-sealed to a polypropylene porous/permeable membrane with a reservoir therebetween. The patch can include a pharmaceutically acceptable adhesive (such as a acrylate, silicone or rubber adhesive) on the membrane layer to adhere the patch to the skin of the host, e.g., a mammal such as a human. A release liner such as a polyester release liner can also be provided to cover the adhesive layer prior to application of the patch to the skin as is conventional in the art. This patch assembly can be packaged in an aluminum foil or other suitable pouch, again as is conventional in the art.

Alternatively, the capsaicin formulation can be formulated into a "matrix-type" transdermal patch. *Drug Delivery Systems Characteristics and Biomedical Application*, R. L Juliano, ed., Oxford University Press. N.Y. (1980); and *Controlled Drug Delivery*, Vol. I Basic Concepts, Stephen D. Bruck (1983) describe the theory and application of methods useful for transdermal delivery systems. The relevant teachings of these texts are herein incorporated by reference. The drug-matrix could be formed utilizing various polymers, e.g. silicone, polyvinyl alcohol. The "drug matrix" may then be packaged into an appropriate transdermal patch.

A third type of patch comprises incorporating the drug directly in a pharmaceutically acceptable adhesive and laminating the drug-containing adhesive onto a suitable backing member, e.g. a polyester backing membrane. The drug should be present at a concentration which will not affect the adhesive properties, and at the same time deliver the required clinical dose.

The expected side effects of the high dose application of the capsaicin composition are believed to be from intense C fiber discharge occurring during the excitatory phase before C fiber desensitization. However, the prior administration of an anesthetic, such as tetracaine, proximal to the site of application in accordance with the invention, eliminates or substantially abates such side effects. If some "breakthrough pain" occurs despite the anesthetic, then this pain may be treated by administering an analgesic such as a narcotic analgesic (e.g., the various alkaloids of opium, such as morphine, morphine salts, and morphine analogs such as fentanyl, normorphine, or dilaudid and so forth).

Patients given only anesthetic did not experience pain relief beyond the expected duration of the anesthetic. Because the patient in the following example describes long term pain relief much beyond the expected duration of the regional anesthetic, this relief cannot be due to the action of the anesthetic alone and is due to the combination of the block and capsaicin (since administration of the high concentration capsaicin without the anesthetic would not be possible). As will be described, application of high dose capsaicin combined with a prior administration of a regional anesthetic appears to be an extremely effective therapy for treating resistant neuropathic pain.

EXAMPLE 1

A 77 year old white male complained of a 9 month history of postherpetic neuralgia involving the left foot and medial calf. He was unable to tolerate oral medications including opiates, anticonvulsants, and trycyclics secondary to sedation and nausea.

He received ELMA™ cream to both the dorsal and plantar surfaces of his foot. After 90 minutes, C fiber function was evaluated on the foot and found to be significantly attenuated. 7.5% topical capsaicin was then applied by patch for 60 minutes. He began to experience burning after 45 minutes, which responded to intravenous fentanyl.

The capsaicin was removed and he reported numbness at the site of the treatment. Two hours later, sensation had completely returned. He experienced more burning which responded to oral morphine. Five days later, he reported 75% reduction in his pain from postherpetic neuralgia. Eight weeks later he reported greater than 80% ongoing pain relief.

It is to be understood that while the invention has been described above in conjunction with preferred specific embodiments, the description and example is intended to illustrate and not limit the scope of the invention, which is defined by the scope of the appended claims.

It is claimed:

1. A device for treatment of neuropathic pain in a human patient, said device comprising:
   a skin-adherent patch, the patch including a reservoir comprising a therapeutic formulation whereby said formulation is continuously provided to the surface of skin for a predetermined period of time, wherein said formulation comprises capsaicin or a capsaicin analog in a total concentration from greater than about 5% to 10% by weight of the formulation, wherein a single administration of said patch affords significant relief of said neuropathic pain to said human patient for at least several weeks.

2. The device as in claim 1 wherein the formulation is therapeutically effective in treating neuropathic pain in a human patient when the area being treated has first been effectively anesthetized so as to block afferent nerve fibers.

3. The device as in claim 2 further comprising a second patch, the second patch capable of delivering an anesthetic in an amount effective to block afferent nerve fibers to the side effects of the capsaicin or capsaicin analog administered via the patch.

4. The device as in claim 1 wherein the total concentration of the capsaicin or capsaicin analog is about 7.5 weight percent to 10 weight percent.

5. The device as in claim 1, wherein said capsaicin or a capsaicin analog is capsaicin.

* * * * *